US012778615B2

(12) United States Patent
Calvo et al.

(10) Patent No.: US 12,778,615 B2
(45) Date of Patent: Nov. 3, 2026

(54) DEVICES, SYSTEMS, AND METHODS FOR GRASPING TISSUE

(71) Applicant: BOSTON SCIENTIFIC SCIMED, INC., Maple Grove, MN (US)

(72) Inventors: Yeison Calvo, San Ramón (CR); Sean P. Fleury, Princeton, MA (US); Gian Franco Loo Fuchs, San Jose (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 222 days.

(21) Appl. No.: 18/229,260

(22) Filed: Aug. 2, 2023

(65) Prior Publication Data

US 2024/0041487 A1 Feb. 8, 2024

Related U.S. Application Data

(60) Provisional application No. 63/394,747, filed on Aug. 3, 2022.

(51) Int. Cl.
*A61B 17/28* (2006.01)
*A61B 17/00* (2006.01)
*A61B 17/30* (2006.01)

(52) U.S. Cl.
CPC ............ *A61B 17/282* (2013.01); *A61B 17/30* (2013.01); *A61B 2017/00526* (2013.01); *A61B 2017/00867* (2013.01)

(58) Field of Classification Search
CPC ....... A61B 17/28; A61B 17/282; A61B 17/29; A61B 17/30; A61B 2017/00526; A61B 2017/00867; A61B 2017/2926; A61B 2017/2932; A61B 90/03; A61B 2090/032
See application file for complete search history.

(56) References Cited

U.S. PATENT DOCUMENTS

| | | | | |
|---|---|---|---|---|
| 5,499,998 | A | 3/1996 | Meade | |
| 5,620,459 | A | 4/1997 | Lichtman | |
| 5,964,779 | A * | 10/1999 | Mayenberger | A61B 17/29 606/174 |
| 2004/0172057 | A1* | 9/2004 | Guillebon | A61B 17/29 606/207 |

(Continued)

FOREIGN PATENT DOCUMENTS

EP 0888746 A2 1/1999

OTHER PUBLICATIONS

International Search Report and Written Opinion dated Oct. 24, 2023 for International Application No. PCT/US2023/029263.

*Primary Examiner* — Robert A Lynch
(74) *Attorney, Agent, or Firm* — Seager, Tufte & Wckhem, LLP

(57) ABSTRACT

An end effector having first and second jaws movable between an open configuration and a closed configuration. At least one jaw has a tissue-engaging surface contoured to enhance grasping of tissue between the jaws. For instance, the tissue-engaging surfaces may be contoured to engage tissue along the tissue-engaging surface substantially evenly/uniformly and/or contemporaneously from the distal end to the proximal end of the jaw. The tissue-engaging surfaces may be contoured independently of and/or differently from the jaw's outer surface. The tissue-engaging surfaces of the first and second jaws may be contoured to enclose tissue engaged therebetween.

15 Claims, 3 Drawing Sheets

(56) References Cited

U.S. PATENT DOCUMENTS

| | | | | |
|---|---|---|---|---|
| 2017/0281263 | A1* | 10/2017 | Batchelor .............. | A61B 17/30 |
| 2019/0298401 | A1* | 10/2019 | Gupta .................... | A61B 90/30 |
| 2020/0054317 | A1* | 2/2020 | Pisarnwongs ...... | A61B 17/0485 |

* cited by examiner

DEVICES, SYSTEMS, AND METHODS FOR GRASPING TISSUE

CROSS-REFERENCE TO RELATED APPLICATIONS

This application claims the benefit of priority under 35 U.S.C. § 119 to U.S. Provisional Application No. 63/394,747, filed Aug. 3, 2022, the entire disclosure of which is hereby incorporated by reference herein for all purposes.

FIELD

The present disclosure relates generally to the field of medical devices, systems, and methods. In particular, the present disclosure relates to medical devices, systems, and methods for grasping and/or manipulating tissue.

BACKGROUND

Various medical, surgical, laparoscopic, endoscopic, etc., procedures involve grasping and/or manipulating anatomical structures and/or tissues with a tissue-grasping device, such as may be known to those of ordinary skill in the art as an end effector. It is important to achieve secure engagement of the tissue between arms or jaws of the end effector so that the tissue does not slip out from the grasp of the end effector. Reduction of tissue slippage from end effector arms is therefore an ongoing need in the art. Moreover, it is generally desirable to distribute forces along the grasped tissue so that the grasped tissue and/or anatomical structure is not damaged by the grasping force of the end effector. Improvements to end effectors accordingly would be welcome in the art.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, an end effector includes a first jaw having a proximal end and a distal end, a tissue-facing side extending between the proximal end and the distal end and defining a tissue-engaging surface, and an outer side extending between the proximal end and the distal end and defining an outer surface; and a second jaw having a proximal end and a distal end, a tissue-facing side extending between the proximal end and the distal end and defining a tissue-engaging surface, and an outer side extending between the proximal end and the distal end and defining an outer surface. In some aspects, the proximal ends of the first jaw and the second jaw are coupled together with the tissue-facing sides thereof facing each other and the outer sides thereof facing away from each other; the distal ends of the first jaw and the second jaw are movable between an open configuration spaced apart from each other and a closed configuration adjacent each other; and the tissue-engaging surfaces of the first jaw and the second jaw are contoured independently of the outer surfaces to distribute forces evenly across tissue grasped by the jaws.

In some embodiments, the tissue-engaging surface of at least one of the jaws is concavely contoured. In some embodiments, the tissue-engaging surfaces of both the first jaw and the second jaw are concavely contoured to form a tissue-engaging space therebetween. In some embodiments, the outer surface of the at least one of the jaws is substantially straight.

In some embodiments, the distance between the tissue-engaging surfaces of the jaws increases from the distal ends to the proximal ends of the jaws to distribute forces evenly across tissue grasped between the jaws.

In some embodiments, the tissue-engaging surface of at least one of the jaws includes a plurality of spaced apart projections. In some embodiments, the plurality of spaced apart projections are contoured to distribute forces evenly across tissue grasped by the jaws. In some embodiments, the tissue-engaging surfaces of both the jaws include a plurality of spaced apart projections, tissue-engaging surfaces of projections on the first jaw being increasingly spaced apart from tissue-engaging surfaces of projections on the second jaw from the distal end of the jaws to the proximal ends of the jaws. In some embodiments, the spaced-apart projections on the jaws comprise substantially square spaced-apart teeth. In some embodiments, the plurality of spaced apart projections are contoured to atraumatically engage tissue.

In some embodiments, the jaws are biased apart from each other into an open configuration.

In some embodiments, the first jaw and the second jaw are formed by cutting a wire formed from a shape-memory to define opposed tissue-engaging surfaces of the first jaw and the second jaw.

In some embodiments, the jaws are pivotably coupled together.

In accordance with various principles of the present disclosure a system for grasping tissue includes an end effector, a tubular member; and an actuator coupled to the end effector to move the end effector with respect to the tubular member to shift the first and second jaws between the open and closed configurations. In some aspects, the end effector has a first jaw having a proximal end and a distal end, a tissue-facing side extending between the proximal end and the distal end and defining a tissue-engaging surface, and an outer side extending between the proximal end and the distal end and defining an outer surface; and a second jaw having a proximal end and a distal end, a tissue-facing side extending between the proximal end and the distal end and defining a tissue-engaging surface, and an outer side extending between the proximal end and the distal end and defining an outer surface. In some aspects, the proximal ends of the first jaw and the second jaw are coupled together with the tissue-facing sides thereof facing each other and the outer sides thereof facing away from each other; the distal ends of the first jaw and the second jaw are movable between an open configuration spaced apart from each other and a closed configuration adjacent each other; and the tissue-engaging surfaces of the first jaw and the second jaw are contoured independently of the outer surfaces to distribute forces evenly across tissue grasped by the jaws. In some embodiments, the tissue-engaging surfaces of the jaws are moved toward each other upon moving the jaws into the tubular member, wherein the tubular member applies a closing force to the jaws, and the closing force is substantially evenly distributed by the tissue-engaging surfaces across tissue grasped by the jaws.

In accordance with various principles of the present disclosure, a method of forming an end effector includes contouring a tissue-engaging surface of at least the first jaw of the end effector independently of an outer surface of the first jaw of the end effector; and coupling the proximal end of the first jaw to the proximal end of the second jaw with the tissue-engaging surface of the first jaw facing a tissue-engaging surface of the second jaw so that the distal ends of the first jaw and the second jaw are movable between an open configuration in which the tissue-engaging surfaces of the first and second jaws are spaced apart to allow tissue to positioned therebetween, and a closed configuration in which the tissue-engaging surfaces engage tissue positioned therebetween. In some embodiments, contouring of the tissue-engaging surface includes designing the contour to distribute forces evenly across tissue grasped between the first jaw and the second jaw as the proximal ends move from the open configuration to the closed configuration with tissue positioned between the first jaw and the second jaw.

In some embodiments, the method includes contouring the tissue-engaging surface of the first jaw so that the distance of the tissue-engaging surface from the outer surface of the first jaw increases from the proximal end to the distal end of the first jaw. In some embodiments, the method includes contouring the tissue-engaging surfaces of the first jaw and the second jaw as a plurality of projections spaced apart from one another by gaps, wherein the distances of tissue engaging surfaces of the projections of the opposed first jaw and second jaw decrease from the distal ends of the first jaw and the second jaw to the proximal ends of the first jaw and the second jaw.

In some embodiments, the method includes contouring the tissue-engaging surfaces of at least the first jaw to form a generally concave tissue engaging surface from the distal end to the proximal end of the first jaw, without contouring the outer surface of the first jaw.

In some embodiments, the method includes forming the first jaw and the second jaw by cutting a rod from a distal end thereof toward a proximal end thereof, the cut defining the tissue-engaging surfaces of the first jaw and the second jaw.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
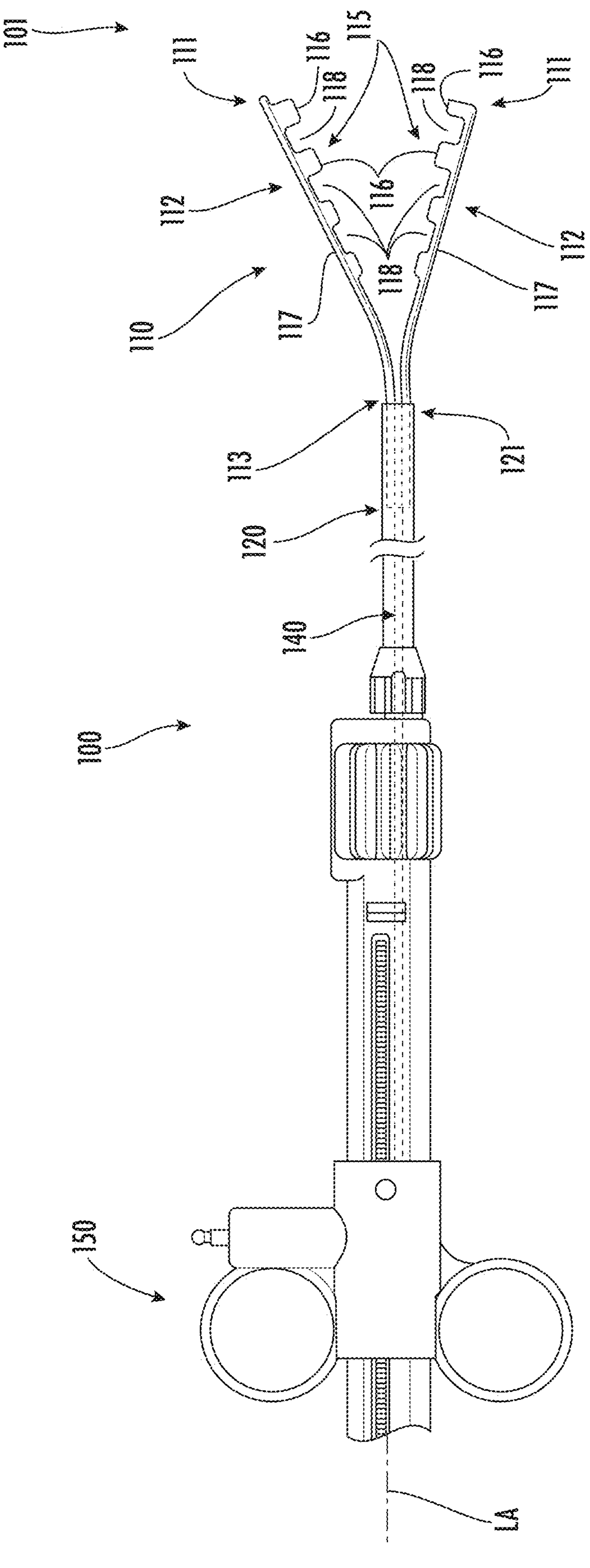
FIG. 1 illustrates an elevational view of tissue-grasping system formed in accordance with aspects of the present disclosure.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably herein without intent to limit, and including automated controller systems or otherwise), etc., such as when using a device (e.g., introducing the device into a patient, or during implantation, positioning, or delivery), and/or closest to a delivery device, and “distal” refers to the direction or location furthest from the user, such as when using the device (e.g., introducing the device into a patient, or during implantation, positioning, or delivery), and/or closest to a delivery device. “Longitudinal” means extending along the longer or larger dimension of an element. A “longitudinal axis” extends along the longitudinal extent of an element, though is not necessarily straight and does not necessarily maintain a fixed configuration if the element flexes or bends. “Central” means at least generally bisecting a center point and/or generally equidistant from a periphery or boundary, and a “central axis” means, with respect to an opening or an element, a line that at least generally bisects a center point of the opening or element, extending longitudinally along the length of the opening or element. As used herein, a “free end” of an element is a terminal end at which such element does not extend beyond.

The present disclosure relates to improvements to tissue-grasping surfaces of medical devices, systems, instruments, etc., and is not limited by the details of the device, system, or instrument with such tissue-grasping surfaces. For the sake of convenience, and without intent to limit, reference is made to an end effector as the device, or component of a device, system, or instrument, etc., with tissue-engaging surfaces. For the sake of convenience and without intent to limit, the end effector is described herein as having arms or jaws or legs on which tissue-engaging surfaces are formed in accordance with various principles of the present disclosure. It will be appreciated that terms such as device, system, instrument, etc., are used in a non-limiting manner herein, and may be used interchangeably herein without intent to limit.

In accordance with various principles of the present disclosure, an end effector is configured to grab and hold tissue securely and to overcome tendency of the tissue to slip from the end effector’s grasping arms. In some aspects of the present disclosure, the jaws of the end effector apply force substantially evenly/uniformly across the tissue being grasped. Uniform application of force to the tissue being grasped may increase the ability of the device and associated system to overcome any slippage of the tissue therefrom. It will be appreciated that terms such as grasp, grab, hold, manipulate, maneuver, etc., and other grammatical forms thereof, may be used interchangeably herein without intent to limit. Moreover, it will be appreciated that reference may be made to tissue, anatomical structures, organs, vessels, etc., interchangeably herein and without intent to limit.

In some aspects, an end effector includes a pair of arms or jaws or legs (such terms being used interchangeably herein without intent to limit) movable with respect to each other to grasp tissue therebetween. In an open configuration of the end effector, tissue may enter between the end effector arms, and in a closed configuration of the end effector, the tissue may be grasped or held by the end effector arms. Each end effector arm thus has a tissue-engaging surface facing a tissue-engaging surface of the other end effector arm. Each end effector arm also has an outer surface facing away from its tissue-engaging surface and away from the other end effector arm. The contour of the tissue-engaging surfaces of jaws of end effectors formed in accordance with various principles of the present disclosure may be formed to provide various enhancements over prior end effectors, as described herein. It will be appreciated that references to tissue-engaging surfaces herein are to be understood as applying to one or both of the jaws of an end effector unless otherwise indicated, regardless of whether reference is made to the singular or plural form of such element.

In accordance with various principles of the present disclosure, the tissue-engaging surfaces are configured and/or contoured such that closing of the jaws onto the tissue distributes forces substantially evenly across the tissue for a firm hold on the tissue, resisting slippage of the tissue from the jaws. It may be appreciated that the more evenly forces are distributed across the tissue, the better the jaws are able to resist slippage of the tissue therefrom. It will be appreciated that reference may be made to terms such as even, uniform, etc., and other grammatical forms thereof, interchangeably herein and without intent to limit. In some embodiments, the jaws are biased apart from each other into an open configuration, and drawn together and closed, such as by being proximally retracted into a tubular element. Tissue-engaging surfaces of such jaws may be formed in accordance with various principles of the present disclosure to grasp tissue and to counteract slippage of the tissue with respect thereto. More particularly, in embodiments of end effectors in which the jaws are drawn into a tubular member to be moved into a closed configuration to grasp tissue, the jaws grasp (e.g., compress) as well as pull tissue as the jaws are being closed. The tissue-engaging surfaces may be formed in accordance with various principles of the present disclosure to counteract slippage of the tissue as the tissue is being pulled and compressed against the tubular element into which the jaws are withdrawn. For instance, the contour of the tissue-engaging surfaces may be designed in accordance with various principles of the present disclosure so that upon closing the end effector jaws, a sufficient amount of force is applied evenly across the grasped tissue to overcome resistance of the tissue to being grasped and pulled.

The tissue-engaging surfaces of end effectors formed in accordance with various principles of the present disclosure may be configured to engage tissue generally substantially uniformly/equally from the proximal end to the distal end of the jaws as the jaws are closed onto tissue positioned therebetween. Additionally or alternatively, the tissue-engaging surfaces may be configured to engage the tissue generally substantially contemporaneously from the proximal end to the distal end of the jaws as the jaws are closed onto tissue positioned therebetween. Such engagement is in contrast with the engagement of tissue by prior end effector jaws without specially-contoured tissue-engaging surfaces and which may have proximal ends which engage tissue before the distal ends engage the tissue as the jaws are closed, and which may thus cause the tissue to be pushed distally out from between the jaws. For instance, prior/currently available scissor-like end effectors have pivotably connected arms with tissue-engaging surfaces near the pivot point of the arms which typically engage tissue before the tissue-engaging surfaces near the distal ends of the arms engage tissue. In contrast, the tissue-engaging surfaces of end effector arms formed in accordance with various principles of the present disclosure may be configured to approach and engage tissue substantially at the same time and/or rate along the length of the end effector arms as the end effector arms are brought together. For instance, the distance between the tissue-engaging surfaces of the end effector arms when in a closed configuration (e.g., defining a tissue-engaging space generally transverse to the length of the end effector arms) may increase along the length of the end effector arms from the distal ends to the proximal ends thereof. As referenced herein, the length of the end effector arms is to be understood as extending from the proximal ends (at which the end effector arms typically are coupled) to the distal ends (free ends of the arms which are spaced apart when the end effector is in an open configuration) of the end effector arms. As such, although the arms of the end effector may be joined together along the proximal end of the end effector with the distal ends spaced apart from each other when the end effector is in an open configuration, the increased distance between the tissue-engaging surfaces at the proximal ends of the end effector arms relative to the decreased distance between the tissue-engaging surfaces at the distal ends of the end effector arms generally allows the tissue-engaging surfaces along the lengths of the end effector arms to engage tissue generally contemporaneously as the end effector arms are drawn together from an open configuration to a closed configuration. In other words, the decreasing distance between the tissue-engaging surfaces of the end effector arms in a proximal-to-distal direction when the end effector is in a closed configuration allows the distal ends of the end effector arms to contact/engage tissue sooner than would be achieved in prior art end effectors (in which the distance between the tissue-engaging surfaces thereof do not vary along the length of the arms thereof).

Additionally or alternatively, end effectors formed in accordance with various principles of the present disclosure may be configured to enclose the grasped tissue between the tissue-engaging surfaces extending between the proximal ends and the distal ends of the end effector arms. More particularly, in some embodiments, when the end effector arms are moved to a closed configuration, the tissue-engaging surfaces thereof may contact each other at distal ends thereof, or at least may be closer together than more-proximal portions of the end effector arms at least when the end effector arms are in a closed position. As such, tissue is held within the tissue-engaging space between the end effector arms and defined by the tissue-engaging surfaces thereof between the proximal ends and the closed (or closer) distal ends. In some embodiments, the tissue-engaging surfaces are spaced increasingly further apart from the distal ends of the end effector arms to the proximal ends of the end effector arms. As such, the tissue-engaging surfaces of the end effector arms face each other to form an enclosed (or at least partially-enclosed) tissue-engaging space between the end effector arms.

In some embodiments, the tissue-engaging surfaces of an end effector formed in accordance with various principles of the present disclosure may be formed in a generally concave configuration. End effectors with one or more jaws having a tissue-engaging surface with a generally concave contours may serve to enclose tissue between the proximal ends and the distal ends of the end effector jaws. In some instance, such shape may capture the tissue between the jaws so that the jaws may move the tissue without the tissue slipping out from between the jaws. Additionally or alternatively, such shape may distribute forces substantially evenly across the tissue, thereby improving resistance to slippage of tissue engaged thereby (e.g., by uniformly increasing friction with respect to such tissue). In some embodiments, such contour applies a sufficient amount of force to the tissue being grasped to overcome slippage. More particularly, because the tissue-engaging surfaces are increasingly closer together from the proximal ends of the jaws to the distal ends of the jaws of the end effector, the tissue-engaging surfaces of the opposed jaws generally approach each other contemporaneously across the full length of the tissue-engaging surfaces between the proximal and distal ends of the jaws.

In some embodiments, the tissue-engaging surfaces are formed as teeth which increase in height (in a direction transverse to the longitudinal axis of the end effector) from the proximal end to the distal end thereof. In other words, there is an increasingly larger distance between surfaces of the teeth forming the tissue-engaging surfaces of the arms from the distal end to the proximal end of the end effector. Such increase allows tissue to be engaged by the proximal tissue-engaging surfaces without being “squished” or pushed distally outward as the end effector is moved to a closed configuration. Also, the increase in the length of the teeth from the proximal ends to the distal ends of the end effector counters the effect of the increase in distance from the end effector arms as the arms are opened to grab tissue therebetween. As such, as the end effector is moved to a closed configuration, the teeth at the distal ends of the end effector arms engage tissue even though such ends are further apart than the proximal ends of the end effector arms. The overall contour of such teeth may present a generally concave surface to tissue grasped between the end effector jaws.

Various embodiments of end effectors, jaws of end effectors, and devices, systems, and methods for grasping tissue will now be described with reference to examples illustrated in the accompanying drawings. Reference in this specification to “one embodiment,” “an embodiment,” “some embodiments”, “other embodiments”, etc. indicates that one or more particular features, structures, concepts, and/or characteristics in accordance with principles of the present disclosure may be included in connection with the embodiment. However, such references do not necessarily mean that all embodiments include the particular features, structures, concepts, and/or characteristics, or that an embodiment includes all features, structures, concepts, and/or characteristics. Some embodiments may include one or more such features, structures, concepts, and/or characteristics, in various combinations thereof. It should be understood that one or more of the features, structures, concepts, and/or characteristics described with reference to one embodiment can be combined with one or more of the features, structures, concepts, and/or characteristics of any of the other embodiments provided herein. That is, any of the features, structures, concepts, and/or characteristics described herein can be mixed and matched to create hybrid embodiments, and such hybrid embodiment are within the scope of the present disclosure. Moreover, references to “one embodiment,” “an embodiment,” “some embodiments”, “other embodiments”, etc. in various places in the specification are not necessarily all referring to the same embodiment, nor are separate or alternative embodiments necessarily mutually exclusive of other embodiments. It should further be understood that various features, structures, concepts, and/or characteristics of disclosed embodiments are independent of and separate from one another, and may be used or present individually or in various combinations with one another to create alternative embodiments which are considered part of the present disclosure. Therefore, the present disclosure is not limited to only the embodiments specifically described herein, as it would be too cumbersome to describe all of the numerous possible combinations and subcombinations of features, structures, concepts, and/or characteristics, and the examples of embodiments disclosed herein are not intended as limiting the broader aspects of the present disclosure. The following description is of illustrative examples of embodiments only, and is not intended as limiting the broader aspects of the present disclosure.

In the drawings, it will be appreciated that common features are identified by common reference elements and, for the sake of brevity and convenience, and without intent to limit, the descriptions of the common features are generally not repeated. For purposes of clarity, not all components having the same reference number are numbered. Moreover, a group of similar elements may be indicated by a number and letter, and reference may be made generally to one or such elements or such elements as a group by the number alone (without including the letters associated with each similar element). It will be appreciated that, in the following description, elements or components similar among the various illustrated embodiments with reference numbers greater than 100 are generally designated with the same reference numbers increased by a multiple of 100 and redundant description is generally omitted for the sake of brevity. Moreover, certain features in one embodiment may be used across different embodiments and are not necessarily individually labeled when appearing in different embodiments. For the sake of brevity and convenience, and without intent to limit, common elements with common functions are indicated with the same reference characters differing in value by 100, reference being made to the above descriptions of similar elements and operations.

Figure 2:
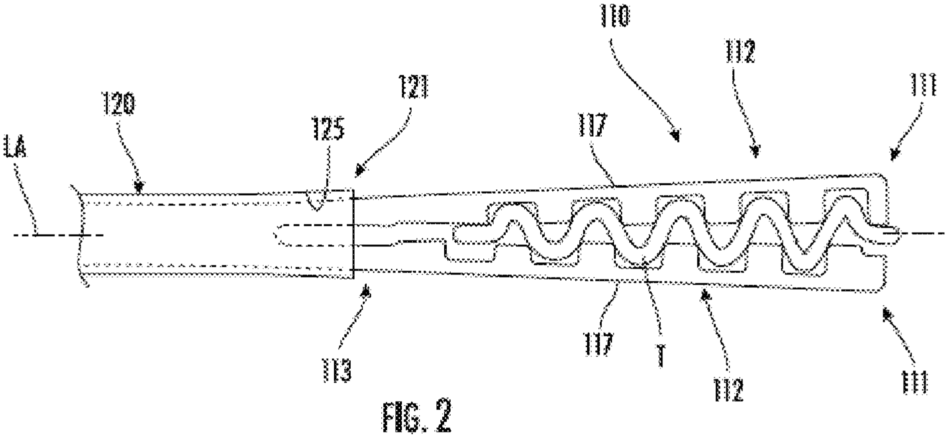
FIG. 2 illustrates an elevational view of an end effector of a tissue-grasping system as in FIG. 1 grasping tissue.

Turning now to the drawings, an example of an embodiment of a tissue-grasping system 100 is illustrated in FIG. 1 in an open configuration, and in FIG. 2 in a closed configuration. The illustrated example of an embodiment of a tissue-grasping system 100 includes an end effector 110 at a distal end 101 of the tissue-grasping system 100 and extending with respect to a tubular member 120. In some embodiments, the proximal end 113 of the end effector 110 is movable with respect to the distal end 121 of the tubular member 120, such as movably coupled with respect to the tubular member 120, as described in further detail below.

The end effector 110 includes a pair of jaws 112 extending distally from the tubular member 120 and movable with respect to each other between an open configuration such as illustrated in FIG. 1, and a closed configuration such as illustrated in FIG. 2. In an open configuration, the distal ends 111 of the jaws 112 are spaced apart from each other (and away from the longitudinal axis LA) to allow tissue or other elements to enter between the tissue-engaging surfaces 115 of the jaws 112. As may be appreciated, the tissue-engaging surfaces 115 of the jaws 112 face each other (e.g., generally toward the longitudinal axis LA of the tissue-grasping system 100), and are defined on tissue-facing sides of the jaws 112 opposite the outer sides along which the outer surfaces 117 of the jaws 112 are defined. The outer surfaces 117 face away from each other (e.g., generally away from the longitudinal axis LA of the tissue-grasping system 100). The end effector 110 illustrated herein is configured to grasp tissue or other elements between the jaws 112. However, the present disclosure is not necessarily limited to tissue, and simply references tissue for the sake of convenience. It will be appreciated that the term jaws may be used interchangeably herein with terms such as arms, grasper arms, graspers, etc., and may be modified by the term grasper or grasping or tissue-grasping etc., without intent to limit.

The end effector 110 may be formed in any desired manner so that the jaws 112 are movable between open and closed configurations. For instance, in the example of an embodiment illustrated in FIG. 3, the end effector 110 may be formed from a rod or wire 130 (e.g., a single monolithic element), dimensioned to allow cutting thereof to form opposed tissue-engaging surfaces 115 of the jaws 112. The material of such end effector 110 may be a flexible material, such as a shape memory material (e.g., Nitinol), allowing flexing of the jaws 112 apart from each other. In the embodiment illustrated in FIG. 3, the jaws 112 may be coupled at proximal ends 113 thereof, and biased apart from each other (from the proximal ends 113 to the distal ends 111 thereof) so that the distal ends 111 of the jaws 112 are spaced apart from each other. In the example of an embodiment illustrated in FIG. 1 and FIG. 2, longitudinal/axial movement (movement generally along the longitudinal axis LA) of the jaws 112 with respect to the tubular member 120 allows or causes the jaws 112 to move between open and closed configurations. For instance, movement of the jaws 112 into and out of a lumen 125 in the tubular member 120 causes the jaws 112 to move to a closed or open configuration, respectively. In the example of an embodiment illustrated in FIG. 1, the end effector 110 is operatively coupled with an actuator 140 (e.g., a pull wire or other such element known to those of ordinary skill in the art) extending to a handle 150 so that operation of the actuator 140 (such as via the handle 140) proximally retracts the jaws 112 with respect to the tubular member 120 or distally advances the jaws 112 away from the tubular member 120 to cause closing or opening of the jaws 112, respectively. The actuator 140 and the handle 150 as well as the manner in which the actuator 140 is coupled with the end effector 110 and the handle 150 may be in any configuration known or heretofore known to those of ordinary skill in the art, the present disclosure not being limited by such features.

Figure 3:
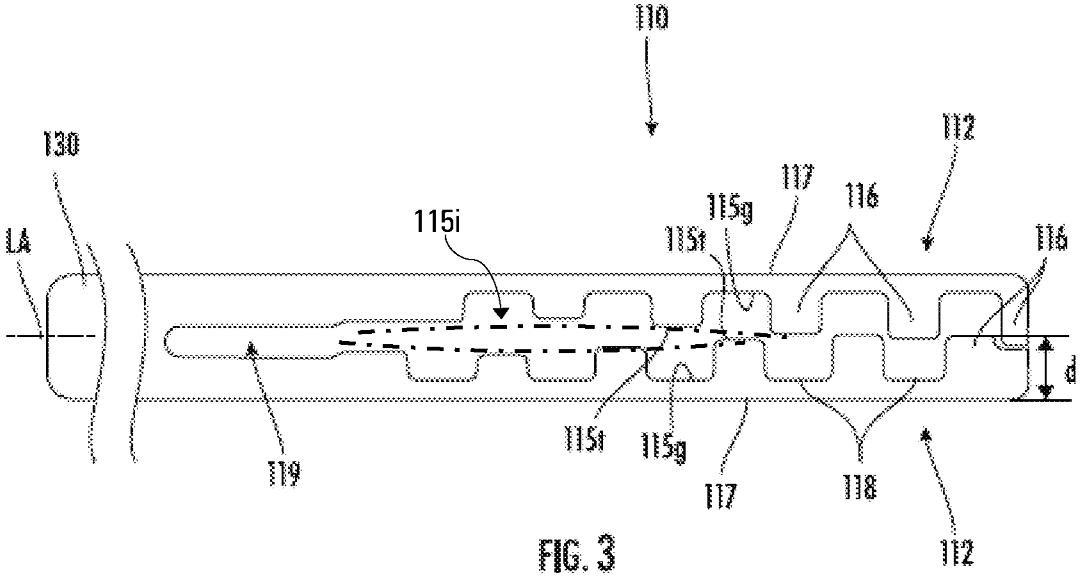
FIG. 3 illustrates an elevational view of an embodiment of an end effector formed in accordance with various principles of the present disclosure.

It will be appreciated that other configurations of tissue-grasping jaws which facilitate closing or opening of the jaws with respect to each other are within the scope and spirit of the present disclosure. For instance, the example of an embodiment illustrated in FIG. 4, the jaws 212 of the end effector 210 are formed separately from each other and are pivotably coupled together about pivot 230. The pivot 230 may be coupled with the actuator 140 in any manner known or heretofore known to those of ordinary skill in the art, the present disclosure not being limited by such features. As may be appreciated, movement of the jaws 212 of the end effector 210 of FIG. 4 with respect to the tubular member 120 effect opening or closing of the jaws 212 in a manner as described above with respect to the jaws 112 illustrated in FIG. 3. Accordingly, reference is made to such description for the sake of brevity and without intent to limit. It will be appreciated that unless otherwise indicated, references herein to features of the example of an embodiment of an end effector 110 illustrated in FIG. 3 are applicable to features of the example of an embodiment of an end effector 210 illustrated in FIG. 4, other than the configuration of the jaws thereof which allow movement of the jaws between the open and closed configurations.

Figure 4:
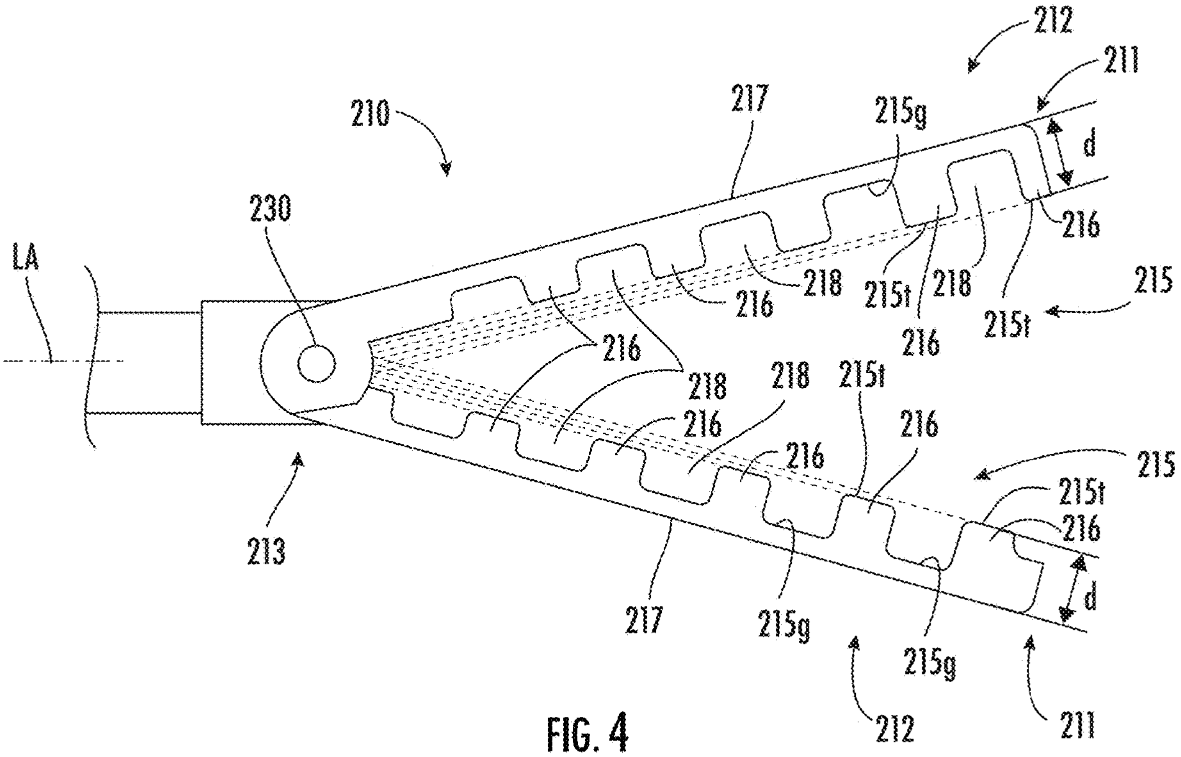
FIG. 4 illustrates an elevational view of another embodiment of an end effector formed in accordance with various principles of the present disclosure.
Figure 5:
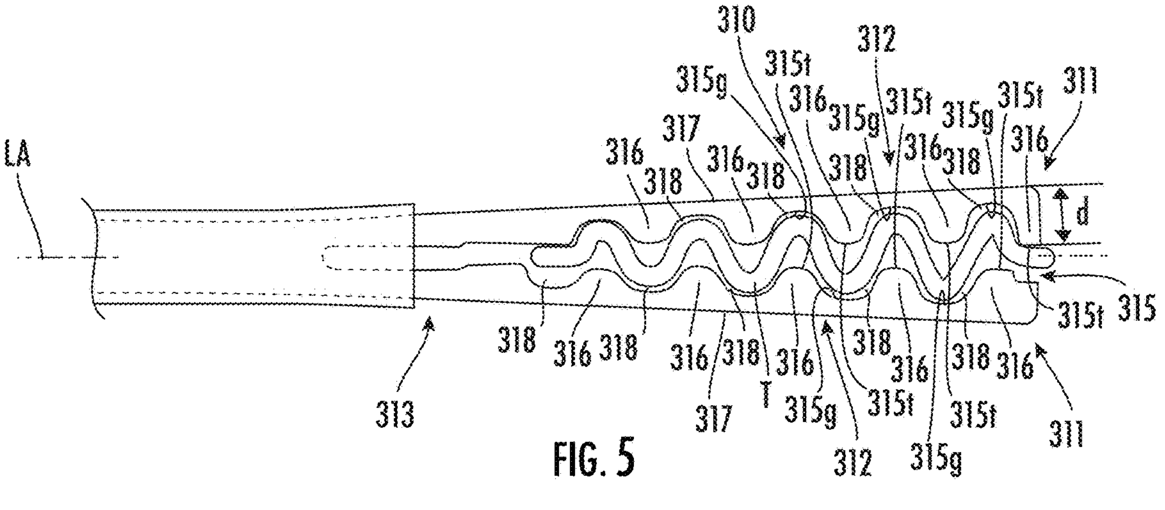
FIG. 5 illustrates an elevational view of another embodiment of an end effector formed in accordance with various principles of the present disclosure and grasping tissue.

An additional example of an embodiment of an end effector 310 is illustrated in FIG. 5, with a different configuration of tissue-engaging surfaces 315 than the tissue-engaging surfaces 115, 215 of the end effectors 110, 210 illustrated in FIGS. 1-5, as described in further detail below. Regardless of the difference between the tissue-engaging surfaces 315 of the end effector 310 illustrated in FIG. 5, other features of the examples of embodiments of end effectors 110, 210 illustrated in FIG. 3 and FIG. 4, respectively, are applicable to the example of an embodiment of an end effector 310 illustrated in FIG. 5.

Once tissue T is positioned between the jaws 112, 212, 312 (when the jaws 112, 212, 312 are in an open configuration), the jaws 112, 212, 312 may be moved to a closed configuration, such as illustrated in FIG. 2, to grasp the tissue T positioned therebetween. In accordance with various principles of the present disclosure, the tissue-engaging surfaces 115, 215, 315 of the jaws 112, 212, 312 are formed not only to grasp tissue securely between the jaws 112, 212, 312, but also to enhance engagement of the tissue-engaging surfaces 115, 215, 315 with respect to the tissue over tissue engagement of prior tissue-engaging surfaces of prior tissue-engaging jaws. For instance, in some aspects, tissue-engaging surfaces 115, 215, 315 of jaws 112, 212, 312 formed in accordance with various principles of the present disclosure are configured to fight against slippage of tissue T grasped between the tissue-engaging surfaces 115, 215, 315 as the end effector 110, 210, 310 is pulled with respect to the tubular member 120 to move the jaws 112, 212, 312 to a closed configuration to grasp tissue T therebetween. Additionally or alternatively, in some aspects, tissue-engaging surfaces 115, 215, 315 of jaws 112, 212, 312 formed in accordance with various principles of the present disclosure are configured to distribute forces substantially evenly across the tissue T grasped therebetween. As such, friction with respect to the tissue T being grasped may thereby be enhanced by the force applied to the tissue, so that even distribution of force improves friction with respect to the end effector arms or jaws and the grasped tissue to reduce slippage of the tissue T from the jaws 112, 212, 312. In some aspects, forces on tissue may be distributed evenly/uniformly as well as substantially contemporaneously by the tissue-engaging surfaces 115, 215, 315 of jaws 112, 212, 312 formed in accordance with various principles of the present disclosure as the jaws 112, 212, 312 move from an open configuration to a closed configuration to grasp the tissue therebetween. In some aspects, the tissue-engaging surfaces 115, 215, 315 approach each other at substantially the same time and/or rate as the jaws 112, 212, 312 are brought together. For instance, even though the overall portion of the jaws 112, 212, 312 along the proximal ends 113, 213, 313 thereof is generally closer to the overall portion of the jaws 112, 212, 312 along the distal ends 111, 211, 311 thereof, the teeth 116, 216, 316 closer to the distal ends 111, 211, 311 are longer than the teeth 116, 216, 316 closer to the proximal ends 113, 213, 313 and thus make up for the difference in distance between the jaws 112, 212, 312 (e.g., the outer surfaces 117, 217, 317 of the jaws 112, 212, 312). Furthermore, in some aspects, tissue-engaging surfaces 115, 215, 315 of jaws 112, 212, 312 may be formed in accordance with various principles of the present disclosure to apply force evenly across the grasped tissue T are less likely to apply excess force along a portion of the grasped tissue T and thus less like to potentially injure the grasped tissue T. Finally, in some aspects, tissue-engaging surfaces 115, 215, 315 of jaws 112, 212, 312 formed in accordance with various principles of the present disclosure may be configured so that the force applied at the proximal ends 113, 213, 313 thereof to close the jaws 112, 212, 312 applies a uniform force along the length of the jaws 112, 212, 312 without the force diminishing significantly from the proximal ends 113, 213, 313 to the distal ends 111, 211, 311 of the jaws 112, 212, 312.

In accordance with various principles of the present disclosure, in some embodiments, the tissue-engaging surfaces 115, 215, 315 of the jaws 112, 212, 312 achieve the desired configuration solely by the shaping or contouring of the tissue-engaging surfaces 115, 215, 315 without also bending, manipulating, curving, deforming, shaping, or otherwise adjusting the overall shape or configuration of the jaws. In other words, the shaping or contouring of the tissue-engaging surfaces 115, 215, 315 may be achieved in accordance with various principles of the present disclosure independently of and without necessarily affecting the overall shape of the jaws 112, 212, 312 and/or the outer surfaces 117, 217, 317. As such, the overall shape of the jaws 112, 212, 312 need not be bent or curved or otherwise formed to define space between the jaws 112, 212, 312 within which tissue T is to be engaged, other than by the shape and/or configuration of the tissue-engaging surfaces 115, 215, 315. In some embodiments, the shape or contour of the tissue-engaging surfaces 115, 215, 315 of the jaws 112, 212, 312 is different from the shape or contour of the outer surfaces 117, 217, 317 of the jaws 112, 212, 312. It will be appreciated that reference may be made herein to terms such as shape, contour, etc., and other grammatical forms thereof, interchangeably and without intent to limit unless otherwise stated.

In some embodiments of end effectors formed in accordance with various principles of the present disclosure, the tissue-engaging surfaces of the jaws of the end effector are contoured so that the distance between the tissue-engaging surfaces increases from the distal ends of the jaws to the proximal ends of the jaws. Examples of embodiments of end effectors 110, 210, 310 with tissue-engaging surfaces 115, 215, 315 with distal ends 111, 211, 311 thereof closer together than proximal ends 113, 213, 313, respectively, are illustrated in FIGS. 1-5. Such configuration of the tissue-engaging surfaces 115, 215, 315 may facilitate retention of grasped tissue T between the jaws 112, 212, 312. Additionally or alternatively, in some embodiments, the overall contour of the tissue-engaging surfaces 115, 215, 315 of at least one of the jaws 112, 212, 312 of end effectors 110, 210, 310 formed in accordance with various principles of the present disclosure may be generally at least partially concave. For instance, in some embodiments, the collective contour of the tissue-engaging surfaces 115, 215, 315 may have generally a generally concave overall contour (along all or part of the longitudinal extent thereof, along the longitudinal axis LA) facing each other. It will be appreciated that the concavity of the collective contour of the tissue-engaging surfaces 115, 215, 315 may be a general, relative concavity, such as by drawing an imaginary line along the tissue-engaging surfaces 115, 215, 315 (such as illustrated by imaginary line 115*i* in FIG. 3), without specific portions of the tissue-engaging surfaces 115, 215, 315 being actually curved. As such, the overall effect of the configurations of the tissue-engaging surfaces 115, 215, 315 is to achieve generally concave tissue-engaging surfaces 115, 215, 315 facing each other between the jaws 112, 212, 312 of the end effectors 110, 210, 310.

As noted above, specific portions of the tissue-engaging surfaces 115, 215, 315 need not be curved (in whole or even in part) in order to achieve an overall concave configuration. In some aspects, the tissue-engaging surfaces 115, 215, 315 of jaws 112, 212, 312 formed in accordance with various principles of the present disclosure are crenulated. For instance, in the examples of embodiments illustrated in FIG. 1-5, the tissue-engaging surfaces 115, 215, 315 of the illustrated examples of embodiments of jaws 112, 212, 312 include teeth 116, 216, 316 generally longitudinally spaced apart by gaps 118, 218, 318. Various configurations of the teeth 116, 216, 316 and gaps 118, 218, 318 may impart a generally concave configuration to the tissue-engaging surfaces 115, 215, 315 of the pairs of jaws 112, 212, 312 of an end effectors 110, 210, 310 formed in accordance with various principles of the present disclosure. Thus, although the teeth 116, 216 and gaps 118, 218 are illustrated as generally square, the present disclosure is not intended to be so limited. For instance, as illustrated in FIG. 5, the teeth 316 and gaps 318 may be curved (e.g., such as wavy or a sine wave).

In some embodiments, such as illustrated in FIG. 3, FIG. 4, and FIG. 5, the heights of the teeth 116, 216, 316 vary from one end of one or both of the jaws 112, 212, 312 to the other end of one or both of the jaws 112, 212, 312. In other words, the distance, in the direction d, of the tissue-engaging surfaces 115*t*, 215*t*, 315*t* of the teeth 116, 216, 316 of the jaws 112, 212, 312 from the outer surfaces 117, 217, 317 varies along the length of the jaws 112, 212, 312, such as by decreasing from the proximal ends 113, 213, 313 of the jaws 112, 212, 312 to the distal ends 111, 211, 311 of the jaws 112, 212, 312 (such as illustrated by the dashed lines in FIG. 4). In some embodiments, the depths of the gaps 118, 218, 318 in the direction d remain substantially constant between the distal ends 111, 211, 311 of the jaws 112, 212, 312 and the proximal ends 113, 213, 313 of the jaws 112, 212, 312. In other embodiments, the depths of the gaps 118, 218, 318 of the opposing jaws 112, 212, 312 of an end effector 110, 210, 310 vary from the distal ends 111, 211, 311 of the jaws 112, 212, 312 to the proximal ends 113, 213, 313 of the jaws 112, 212, 312. In some embodiments, such as in the examples of embodiments illustrated in FIG. 3 and FIG. 4, the tissue-engaging surfaces 115*t*, 215*t* of the teeth 116, 216 of one of an opposed pair of jaws 112, 212 are positioned across from the tissue-engaging surfaces 115*g*, 215*g* of the gaps 118, 218 between the teeth 116, 216 of the other of an opposed pair of jaws 112, 212. Such configuration may improve grasping of tissue between the jaws 112, 212, 312, such as by creating a wavy or tortuous configuration of the tissue grasped by the tissue-engaging surfaces 115, 215, 315 of the jaws 112, 212, 312, such as illustrated in FIG. 2. It will be appreciated that the tissue-engaging surfaces 115*g*, 215*g*, 315*g* of the gaps 118, 218, 318 may or may not engage tissue, depending on the depth of the gaps 118, 218, 318, the shapes of the teeth 116, 216, 316, etc.

In some embodiments, the tissue-engaging surfaces 115*t*, 215*t*, 315*t* of the teeth 116, 216, 316 may be contoured to be atraumatic, such as blunt, convexly-curved or otherwise formed to not damage tissue grasped by the jaws 112, 212, 312. For instance, as illustrated in FIG. 2, and FIG. 3, the teeth 316 may form a curved, somewhat wavy/generally sinusoidal pattern, as illustrated in FIG. 5.

The tissue-engaging surfaces 115, 215, 315 may be contoured, such as to enhance the space created between the jaws 112, 212, 312 and/or the engagement of the tissue-engaging surfaces 115, 215, 315 with the tissue T. For instance, the tissue-engaging surfaces 115, 215, 315 of the jaws 112, 212, 312 may be angled or otherwise contoured to create a generally concave curvature to the overall tissue-engaging surfaces 115, 215, 315 along the longitudinal extent of the jaws 112, 212, 312 (e.g., along an imaginary line drawn along the tissue-engaging surfaces 115, 215, 315, such as illustrated by imaginary line 115*i* in FIG. 3), or at least a portion of such longitudinal extent of the jaws 112, 212, 312.

Additional space 119, 219, 319 (e.g., without teeth or other projections) may be between the jaws 112, 212, 312 to provide additional space for tissue T to be held between the proximal ends 113, 213, 313 of the jaws 112, 212, 312.

As discussed above, in some embodiments, the tissue-engaging surfaces 115, 215, 315 are formed by cutting the surfaces of the material from which the jaws 112, 212, 312 are formed (e.g., cutting a rod 130 in the example of an embodiment illustrated in FIG. 3, or cutting only the surfaces of a pair of jaws 212 which are to face each other, as in the example of an embodiment illustrated in FIG. 4). More particularly, the tissue-engaging surfaces 115, 215, 315 may be formed by a cutting pattern through an end of a rod or wire which separates the rod or wire into jaws 112 such as illustrated in FIG. 3, or by cutting surfaces of separately formed jaws 212 which are coupled together as illustrated in FIG. 4.

In some embodiments, the tissue-engaging surfaces 115, 215, 315 may be contoured differently from the contour of the outer surfaces 117, 217, 317 of the jaws 112, 212, 312. For instance, the tissue-engaging surfaces 115, 215, 315 may form a generally curved (e.g., concave) surface configured to facilitate grasping of tissue between the jaws 112, 212, 312 and/or to allow space for tissue T to fit between the jaws 112, 212, 312, and/or have other or additional features or characteristics, whereas the outer surfaces of the jaws 112 may be straight.

As noted above, it will be appreciated that various features described above may be applied to both or only one of a pair of jaws of an end effector formed in accordance with various principles of the present disclosure.

Principles of the present disclosure may be applied to various medical devices, instruments, tools, etc., such as, without limitation, a variety of medical devices for grasping, manipulating, moving, engaging, or otherwise interacting with various anatomical structures. It will be appreciated that other configurations of the tissue-engaging surfaces to suit the end use of the end effector 110, such as to engage a particular type of tissue or other element, are with the scope and spirit of the present disclosure, the embodiments described above being examples of embodiments and not intended to limit broad principles of the present disclosure.

It will be appreciated that all apparatuses and methods discussed herein are examples of apparatuses and/or methods implemented in accordance with one or more principles of this disclosure. These examples are not the only way to implement these principles but are merely examples, not intended as limiting the broader aspects of the present disclosure. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

It will be appreciated features described with respect to one embodiment typically may be applied to another embodiment, whether or not explicitly indicated. The various features hereinafter described may be used singly or in any combination thereof. Therefore, the present invention is not limited to only the embodiments specifically described herein.

Various further benefits of the various aspects, features, components, and structures of end effectors such as described above, in addition to those discussed above, may be appreciated by those of ordinary skill in the art.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. As used in this specification and the appended claims, the term "or" is generally employed in its sense including "and/or" unless the content clearly dictates otherwise. As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, engaged, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the terms "comprises", "comprising", "includes", and "including" do not exclude the presence of other elements, components, features, groups, regions, integers, steps, operations, etc. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. An end effector comprising:

a first jaw having a proximal end and a distal end, a tissue-facing side extending between the proximal end and the distal end and defining a tissue-engaging surface, and an outer side extending between the proximal end and the distal end and defining an outer surface; and a second jaw having a proximal end and a distal end, a tissue-facing side extending between the proximal end and the distal end and defining a tissue-engaging surface, and an outer side extending between the proximal end and the distal end and defining an outer surface;

wherein:

said first jaw and said second jaw are formed of a rod or wire formed from a shape-memory material and cut to define the opposed tissue-engaging surfaces of said first jaw and said second jaw;

the proximal ends of said first jaw and said second jaw are coupled together with the tissue-facing sides thereof facing each other and the outer sides thereof facing away from each other;

the distal ends of said first jaw and said second jaw are movable between an open configuration spaced apart from each other and a closed configuration adjacent each other;

the tissue-engaging surfaces of said first jaw and said second jaw are contoured independently of the outer surfaces to distribute forces evenly across tissue grasped by said jaws;

the distance between the tissue-engaging surfaces of said first jaw and said second jaw increases from the distal ends to the proximal ends of said jaws to distribute forces evenly across tissue grasped between said jaws; and at least one of said jaws defines a tissue-engaging surface from the proximal end to the distal end with a concave contour extending between the proximal end and the distal end to capture tissue between the distal and proximal ends of said jaws.

2. The end effector of claim 1, wherein the tissue-engaging surface portions of the plurality of spaced apart projections of said first jaw collectively define the overall concave contour of the tissue-engaging surface of said first jaw and the tissue-engaging surface portions of the plurality of spaced apart projections of said second jaw collectively define the overall concave contour of the tissue-engaging surface of said second jaw.

3. The end effector of claim 1, wherein the tissue-engaging surfaces of both said first jaw and said second jaw are concavely contoured from the proximal end to the distal end of each said jaw to form a tissue-engaging space between the proximal and distal ends of said first jaw and said second jaw when the first jaw and the second jaw are in the closed configuration.

4. The end effector of claim 1, wherein the outer surface of said at least one of said jaws is substantially straight.

5. The end effector of claim 1, wherein the distance between the tissue-engaging surfaces of said jaws when said jaws are in the closed configuration with the distal ends of said jaws adjacent each other defines a space for tissue to be captured, between the proximal ends of said jaws and the distal ends of said jaws, without compressing or damaging the captured tissue.

6. The end effector of claim 1, wherein the tissue-engaging surface of at least one of said jaws includes a plurality of spaced apart projections which collectively define at least a portion of the overall concave contour of the at least one of said jaws.

7. The end effector of claim 6, wherein said plurality of spaced apart projections are contoured to distribute forces evenly across tissue grasped by said jaws.

8. The end effector of claim 1, wherein said first jaw and said second jaw are formed of a rod or wire formed from a shape-memory material and cut to define the opposed tissue-engaging surfaces of said first jaw and said second jaw.

9. The end effector of claim 1, wherein said plurality of spaced-apart projections on said jaws comprise substantially square spaced-apart teeth.

10. The end effector of claim 1, wherein said plurality of spaced apart projections are contoured to atraumatically engage tissue.

11. The end effector of claim 1, wherein said jaws are biased apart from each other into the open configuration.

12. The end effector of claim 1, wherein said first jaw and said second jaw are movable between the open configuration and the closed configuration by being moved, respectively, out of and into a lumen of a tubular member.

13. The end effector of claim 1, wherein said jaws are pivotably coupled together.

14. A system for grasping tissue, said system comprising:

an end effector comprising:

a first jaw having a proximal end and a distal end, a tissue-facing side extending between the proximal end and the distal end and defining a tissue-engaging surface, and an outer side extending between the proximal end and the distal end and defining an outer surface; and a second jaw having a proximal end and a distal end, a tissue-facing side extending between the proximal end and the distal end and defining a tissue-engaging surface, and an outer side extending between the proximal end and the distal end and defining an outer surface;

wherein:

the proximal ends of the first jaw and the second jaw are coupled together with the tissue-facing sides thereof facing each other and the outer sides thereof facing away from each other;

the distal ends of the first jaw and the second jaw are movable between an open configuration spaced apart from each other and a closed configuration adjacent each other;

the tissue-engaging surfaces of the first jaw and the second jaw are contoured independently of the outer surfaces to distribute forces evenly across tissue grasped by said jaws;

the distance between the tissue-engaging surfaces of said first jaw and said second jaw increases from the distal ends to the proximal ends of said jaws to distribute forces evenly across tissue grasped between said jaws; and at least one of said jaws defines a tissue-engaging surface from the proximal end to the distal end with a concave contour extending between the proximal end and the distal end to capture tissue between the distal and proximal ends of said jaws a tubular member; and an actuator coupled to said end effector to move said end effector with respect to said tubular member to shift said first and second jaws between the open and closed configurations.

15. The system of claim 14, wherein the tissue-engaging surfaces of said jaws are moved toward each other upon moving said jaws into said tubular member, wherein said tubular member applies a closing force to said jaws, and said closing force is configured to be substantially evenly distributed by said tissue-engaging surfaces across tissue grasped by said jaws.

* * * * *